(12) United States Patent
Bouler et al.

(10) Patent No.: US 11,338,054 B2
(45) Date of Patent: May 24, 2022

(54) PHOSPHOCALCIC CEMENT COMPOSITION COMPRISING BLOOD

(71) Applicants:CENTRE NATIONAL DE LA RECHERCHE SCIENTIFIQUE, Paris (FR); UNIVERSITE DE NANTES, Nantes (FR); ONIRIS, Nantes (FR); GRAFTYS, Aix en Provence (FR)

(72) Inventors: Jean-Michel Bouler, Carquefou (FR); Olivier Gauthier, Suce sur Erdre (FR); Bruno Bujoli, Suce sur Erdre (FR); Pascal Janvier, Nantes (FR); Charlotte Mellier, Le Loroux Bottereau (FR)

(73) Assignees: CENTRE NATIONAL DE LA RECHERCHE SCIENTIFIQUE, Paris (FR); UNIVERSITE DE NANTES, Nantes (FR); ONIRIS, Nantes (FR); GRAFTYS, Aix-en-Provence (FR)

( * ) Notice: Subject to any disclaimer, the term of this patent is extended or adjusted under 35 U.S.C. 154(b) by 0 days.

(21) Appl. No.: 16/540,445

(22) Filed: Aug. 14, 2019

(65) Prior Publication Data

US 2019/0365945 A1    Dec. 5, 2019

Related U.S. Application Data

(62) Division of application No. 16/091,957, filed as application No. PCT/EP2017/058293 on Apr. 6, 2017.

(30) Foreign Application Priority Data

Apr. 6, 2016  (EP) .................................. 16305399

(51) Int. Cl.
| | |
|---|---|
| A61F 2/44 | (2006.01) |
| A61L 24/02 | (2006.01) |
| A61L 24/12 | (2006.01) |
| A61L 24/00 | (2006.01) |
| A61L 27/36 | (2006.01) |
| A61L 27/58 | (2006.01) |
| A61K 6/60 | (2020.01) |
| A61K 6/69 | (2020.01) |
| A61K 6/838 | (2020.01) |
| A61K 6/898 | (2020.01) |
| A61B 17/88 | (2006.01) |
| A61L 24/08 | (2006.01) |
| A61B 90/00 | (2016.01) |
| A61B 17/56 | (2006.01) |

(52) U.S. Cl.
CPC .......... *A61L 24/12* (2013.01); *A61B 17/8802* (2013.01); *A61F 2/4455* (2013.01); *A61K 6/60* (2020.01); *A61K 6/69* (2020.01); *A61K 6/838* (2020.01); *A61K 6/898* (2020.01); *A61L 24/001* (2013.01); *A61L 24/0005* (2013.01); *A61L 24/0015* (2013.01); *A61L 24/0042* (2013.01); *A61L 24/02* (2013.01); *A61L 24/08* (2013.01); *A61L 27/365* (2013.01); *A61L 27/3616* (2013.01); *A61L 27/58* (2013.01); *A61B 2017/564* (2013.01); *A61B 2090/3954* (2016.02); *A61B 2090/3966* (2016.02); *A61L 2400/06* (2013.01); *A61L 2430/02* (2013.01); *A61L 2430/12* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 8,389,467 B2 | 3/2013 | Chaput et al. | |
| 2005/0287071 A1* | 12/2005 | Wenz | A61K 33/42 424/9.4 |
| 2011/0224675 A1* | 9/2011 | Tofighi | A61L 24/0015 606/94 |

FOREIGN PATENT DOCUMENTS

| | | |
|---|---|---|
| CN | 101330934 A | 12/2008 |
| CN | 101530630 A | 9/2009 |
| CN | 101 816 807 A | 9/2010 |
| JP | 2004-269393 A | 9/2004 |
| JP | 2011508643 A | 3/2011 |
| JP | 2011087973 A | 5/2011 |
| JP | 2014195712 A | 10/2014 |
| WO | 03053488 A1 | 7/2003 |
| WO | WO 2007/056872 A1 | 5/2007 |
| WO | 2007068489 A2 | 6/2007 |
| WO | 2009087148 A2 | 7/2009 |

OTHER PUBLICATIONS

Sariibrahimoglu K. et al. Tuning the degradation rate of calcium phosphate cements by incorporating mixtures of polylactic-co-glycolic acid microspheres and glucono-delta-lactone microparticles. Tissue Engineering Part A 20.21-22 (2014): 2870-2882. (Year: 2014).*

(Continued)

*Primary Examiner* — Nissa M Westerberg
(74) *Attorney, Agent, or Firm* — Maier & Maier, PLLC

(57) ABSTRACT

A method for promoting spine fusion inside intersomatic cages, comprising placing a fusion cage between two vertebral bodies, and injecting a bone cement paste inside said fusion cage, said bone cement paste containing a powder component comprising α-tricalcium phosphate (α-TCP) particles having an average size greater than or equal to 9 μm, and a liquid component comprising blood.

10 Claims, 6 Drawing Sheets

(56) References Cited

OTHER PUBLICATIONS

Verron E et al. Vertebroplasty using bisphosphonate-loaded calcium phosphate cement in a standardized vertebral body bone defect in an osteoporotic sheep model. Acta biomaterialia. Nov. 1, 2014;10(11):4887-95 (Year: 2014).*
Pioletti DP, Takei H, Lin T, Van Landuyt P, Ma QJ, Kwon SY, Sung KL. The effects of calcium phosphate cement particles on osteoblast functions. Biomaterials. Jun. 1, 2000;21(11):1103-14. (Year: 2000).*
"A basic guide to particle characterization", Malvern Instruments Worldwide, 2015 (Year: 2015).*
Database WPI, Week 201068, Thomas Scientific, London, GB; AN 2010-L95598.
Database WPI, Week 200467, Thomas Scientific, London, GB; AN 2004-682703.
European Search Report received in Application No. 16305399.4, dated Sep. 13, 2016.
International Search Report received in PCT Application No. PCT/EP2017/058293, dated Jun. 12, 2017.
Luis Marchi et al., "Lateral Interbody Fusion for Treatment of Discogenic Low Back Pain: Minimally Invasive Surgical Techniques," Advances in Orthopedics, vol. 16, No. 2, Jan. 1, 2012. pp. 113-117.
N.N., "Grafty HBS," Oct. 14, 2008, (retrieved from internet: http://www.mititalia.it/prodotti/Graftys/Graftys_HBS_comp.pdf).
N.N., "Info: Knochenersatzmaterial," Jan. 28, 2014, (retrieved from internet: http://medical-service-team.com/produkte/download/P113_02_1 GRAFTYSInfoHBSQuicksetBCP.pdf).
Reed Harrison et al., "Mechanical properties of [alpha]-tricalcium phosphate-based bone cements incorporating regenerative biomaterials for filing bone defects exposed to low mechanical loads," Journal of Biomedical Materials Research. Part B: Applied Biomaterials, vol. 104, No. 1, Jan. 10, 2015. pp. 149-157.
Yoshiro Musha et al., "Effects of blood on bone cement made of calcium phosphate: Problems and advantages," Journal of Biomedical Materials Research. Part: Applied Biomaterials, vol. 92B, No. 1, Jan. 1, 2010. pp. 95-101.
Unuma, Hidero, et al. "Preparation of calcium phosphate cement with an improved setting behavior." Journal of Asian Ceramic Societies 1.1 (2013): 26-29.
Sugo, Ken, et al. "Antibiotic elution profile and physical properties of a novel calcium phosphate cement material." Journal of the Ceramic Society of Japan 124.9 (2016): 954-958.
Ginebra, M. P. et al, Biomaterials, 2004, vol. 25, pp. 3453-3462.
Marchi, L. et al., Advances in Orthopedics, 2012, vol. 2012, Article ID 282068, pp. 1-7.
Hirasawa, M. et al., Neurologia Medico-chirurgica (Tokyo), 2014, vol. 54, pp. 722-726.

* cited by examiner

PHOSPHOCALCIC CEMENT COMPOSITION COMPRISING BLOOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application is a divisional of U.S. patent application Ser. No. 16/091,957 filed Oct. 5, 2018, which is the U.S. National Phase under 35 U.S.C. § 371 of International Application No. PCT/EP2017/058293 filed Apr. 6, 2017, designating the U.S. and published as WO 2017/174747 A1 on Oct. 12, 2017, which claims priority to European Patent Application No. 16305399.4 filed Apr. 6, 2016, the disclosure of each of which is incorporated herein in its entirety by reference.

BACKGROUND OF THE INVENTION

Field of the Invention

The present invention concerns a phosphocalcic cement composition comprising blood. The present invention also relates to a method for the preparation of said composition as well as uses of said composition.

Description of the Related Art

The development of synthetic calcium phosphates as bone substitutes is now expanding for decades with the example of porous ceramics that are of very current use in bone surgery, due to their ability to be resorbed in vivo and replaced by natural bone. Injectable calcium phosphate cements (CPCs) are considered as the next generation products, since they offer better primary mechanical properties and give access to implantations under minimally invasive surgery conditions, due to their injectable character. Thus, it is already a few years since several brands of injectable CPCs are available on the market, but substantial improvements are still needed to extend their application and make them suitable for specific clinical indications (e.g. filling of cages for intervertebral fusion, vertebral body augmentation), in particular by increasing their fatigue strength and their osteoconductive properties, among other things.

In order to improve the mechanical properties of CPCs (e.g. higher elasticity), one attractive and intensely investigated route is the introduction of biocompatible and biodegradable fibers or microparticles in the cement formulation, including for example polyesters such as polylactic acid (PLA), poly(lactic-co-glycolic) acid (PLGA) or polycaprolactone (PCL), chitosan (Liu, H. et al., *Acta Biomaterialia* 2006, 2, 557), gelatin (Bigi, A. et al., *Biomaterials* 2004, 25, 2893 and Habraken, W. et al., *Journal Of Biomedical Materials Research Part A* 2008, 87A, 643), collagen (Miyamoto, Y. et al., *Biomaterials* 1998, 19, 707 and Otsuka, M. et al., *J Biomed Mater Res B* 2006, 79B, 176) or polypeptides (Lin, J. P. et al., *Journal Of Biomedical Materials Research Part B-Applied Biomaterials* 2006, 76B, 432). Provided that a good affinity of the bio-degradable polymers towards the inorganic matrix is present, cooperative effects between the two components can indeed be expected as a result of a good transfer of the constraints, at the inorganic/organic interface.

To date, the known calcium phosphate cements have insufficient mechanical properties: they are indeed too fragile and have a too low fatigue strength.

Moreover, these cements have a reduced osteoconductive potential, thus limiting their uses in small volumes.

There is thus a need for phosphocalcic cements with improved mechanical properties and improved osteoconductive potentials.

SUMMARY OF THE INVENTION

The aim of the present invention is thus to provide an injectable phosphocalcic cement having satisfying mechanical properties.

Another aim of the present invention is to provide an injectable phosphocalcic cement having improved mechanical, biological and rheological properties.

The aim of the present invention is also to provide an injectable phosphocalcic cement suitable for bone anchorage or spinal fusion.

Thus, the present invention relates to a bone cement paste containing a powder component comprising α-tricalcium phosphate (α-TCP) particles having an average size greater than or equal to 9 μm, preferably greater than or equal to 10 μm and a liquid component comprising blood or a blood-derived product.

BRIEF DESCRIPTION OF THE DRAWINGS

FIG. 1A contains comparative data and FIG. 1B compares the composition according to the invention (with blood) with a composition without blood.

DETAILED DESCRIPTION

Figure 1:
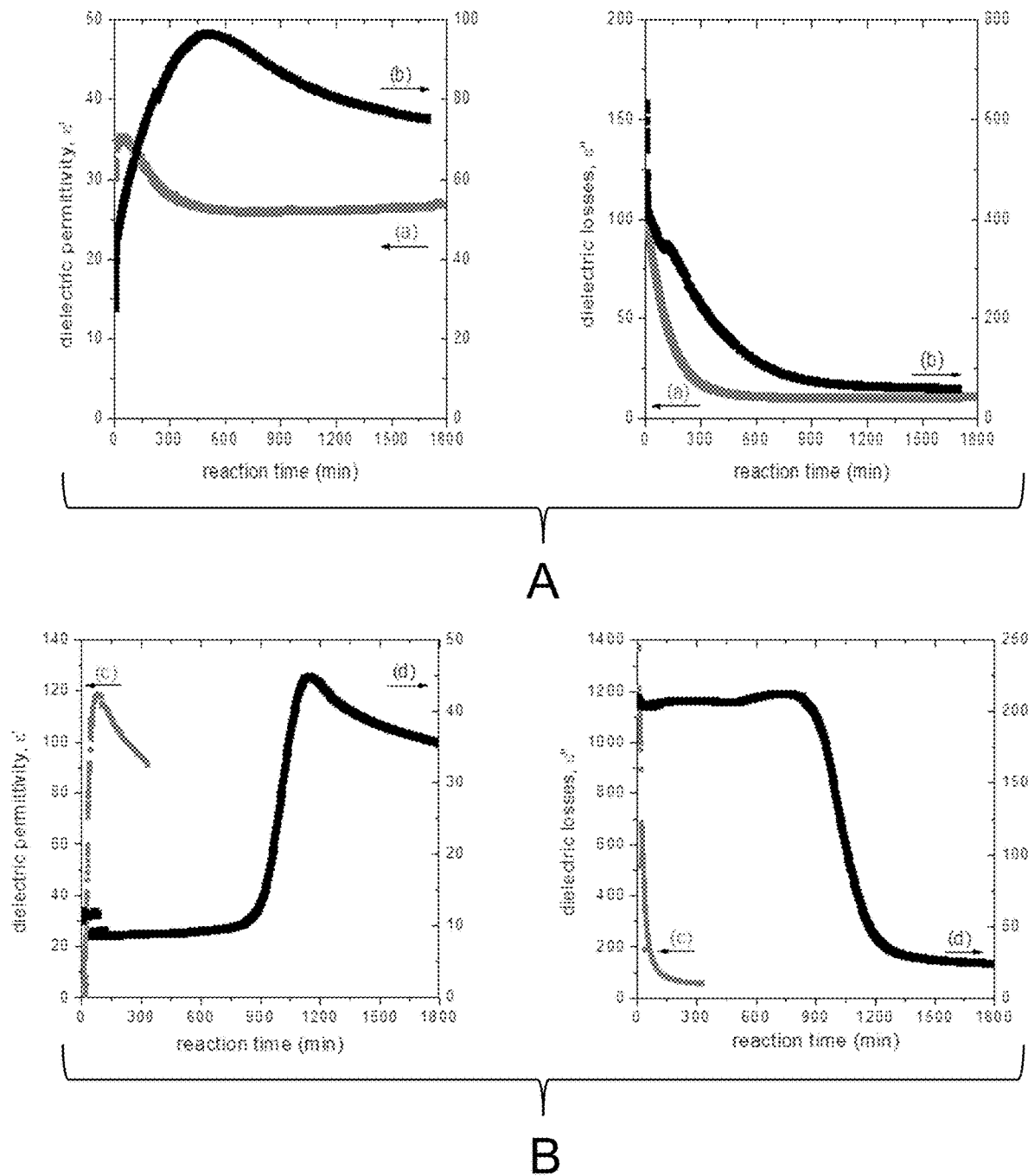
FIG. 1: Variation of dielectric permittivity, ε' (left), and dielectric losses, ε" (right) versus reaction time for (A) QS cement alone (a) and its blood-containing analogue (b); (B) HBS cement alone (c) and its blood-containing analogue (d). Frequency: 10 MHz, temperature: 37° C.

According to an advantageous embodiment, the present invention relates to a bone cement paste containing a powder component comprising α-tricalcium phosphate (α-TCP) particles having an average size greater than or equal to 9 μm, preferably greater than or equal to 10 μm and a liquid component comprising blood.

According to the invention, a "calcium phosphate cement" (or CPC) is a cement wherein the pulverulent solid phase (or powder component) is made of a calcium phosphate compound or a mixture of calcium and/or phosphate compounds.

According to the invention, a "bone cement phase" is a paste obtained from the mixing of a powder component and a liquid component.

In the context of the present invention, the term "phosphocalcic" or "calcium phosphate" refers to minerals containing calcium ions ($Ca^{2+}$) together with orthophosphate ($PO_4^{3-}$), metaphosphate or pyrophosphate ($P_2O_7^{4-}$) and occasionally other ions such as hydroxide ions or protons.

Powder Component

Within the present application, the powder component comprises α-tricalcium phosphate particles having a given average size.

Tricalcium phosphate (TCP) has the formula $Ca_3(PO_4)_2$ and is also known as calcium orthophosphate, tertiary calcium phosphate tribasic calcium phosphate or bone ash. α-TCP has the formula $\alpha\text{-}Ca_3(PO_4)_2$.

The particles of α-TCP according to the invention have an average size greater than or equal to 9 μm, preferably greater than or equal to 10 μm, and more preferably greater than or equal to 11 μm, and even most preferably greater than or equal to 12 μm.

According to an embodiment, the particles of α-TCP according to the invention have an average size greater than 10 μm.

In the context of the present invention, the term "average size" (or "average particle size" or "mean particle size") denotes the mean equivalent diameter of said particles measured by LASER diffraction analysis.

The powder component of the bone cement paste according to the invention comprises α-TCP, said α-TCP being in the form of particles having an average size greater than or equal to 9 μm, preferably greater than or equal to 10 μm as defined above.

According to an embodiment, the particles of α-TCP as defined above have an average size comprised between 9 μm and 100 μm, preferably between 10 μm and 100 μm.

According to an embodiment, the powder component further comprises at least one calcium phosphate compound other than α-TCP.

The powder component of the bone cement paste according to the invention may thus also comprise one or several other calcium phosphate compounds, said compound(s) being different from α-TCP. The powder component may thus comprise α-TCP particles as defined above in combination with at least one other calcium phosphate compound.

Among the calcium phosphate compounds other than α-TCP, one may cite those selected from the group consisting of hydroxyapatite (HA), amorphous calcium phosphate (ACP), monocalcium phosphate anhydrous (MCPA), monocalcium phosphate monohydrate (MCPM), dicalcium phosphate dihydrate (DCPD), dicalcium phosphate anhydrous (DCPA), precipitated or calcium-deficient apatite (CDA), β-tricalcium phosphate (β-TCP), tetracalcium phosphate (TTCP), and mixtures thereof.

According to an embodiment, the powder component comprises α-TCP particles as defined above in combination with a mixture of several different calcium phosphate compounds.

Preferably, the powder component of the bone paste cement according to the invention comprises: α-TCP particles having an average size greater than or equal to 9 μm, preferably greater than or equal to 10 μm, and at least one calcium phosphate compound selected from the group consisting of: MCPA, DCPD, CDA, and mixtures thereof.

In a preferred embodiment, the powder component according to the invention comprises at least 40%, preferably at least 50%, and more preferably at least 60% by weight of α-TCP particles having an average size greater than or equal to 9 μm, preferably greater than or equal to 10 μm, in relation to the total weight of said powder component.

According to an advantageous embodiment, in the bone cement paste according to the invention, the powder component comprises at least 70%, and preferably at least 80%, by weight of α-TCP particles having an average size greater than or equal to 9 μm, preferably greater than or equal to 10 μm, in relation to the total weight of said powder component.

According to an embodiment, the powder component according to the invention consists only of α-TCP particles having an average size greater than or equal to 9 μm, preferably greater than or equal to 10 μm, in relation to the total weight of said powder component. Within such embodiment, the powder component comprises 100% by weight of α-TCP particles having an average size greater than or equal to 9 μm, preferably greater than or equal to 10 μm, in relation to the total weight of said powder component.

According to a preferred embodiment, the powder component according to the invention comprises: α-TCP particles having an average size greater than or equal to 9 μm, preferably greater than or equal to 10 μm, MCPM, CDA, and DPCD.

According to another embodiment, the powder component according to the invention comprises: α-TCP particles having an average size greater than or equal to 9 μm, preferably greater than or equal to 10 μm, CDA, and DPCA.

Preferably, the powder component according to the invention comprises: at least 70%, preferably at least 75%, by weight of α-TCP particles having an average size greater than or equal to 9 μm, preferably greater than or equal to 10 μm, in relation to the total weight of said powder component, at least 5% by weight of CDA in relation to the total weight of said powder component, at least 1% by weight of a mixture of MCPM and DCPD in relation to the total weight of said powder component.

Preferably, the powder component according to the invention comprises: at least 70%, preferably at least 75%, by weight of α-TCP particles having an average size greater than or equal to 9 μm, preferably greater than or equal to 10 μm, in relation to the total weight of said powder component, at least 5% by weight of CDA in relation to the total weight of said powder component, at least 1% by weight of MCPM in relation to the total weight of said powder component, and at least 1% by weight of DCPD in relation to the total weight of said powder component.

Preferably, the powder component according to the invention comprises: at least 70%, preferably at least 75%, by weight of α-TCP particles having an average size greater than or equal to 9 μm, preferably greater than or equal to 10 μm, in relation to the total weight of said powder component, at least 5% by weight of CDA in relation to the total weight of said powder component, and at least 1% by weight of DCPA in relation to the total weight of said powder component.

According to an embodiment, the powder component according to the invention comprises: from 70% to 80% by weight of α-TCP particles having an average size greater than or equal to 9 μm, preferably greater than or equal to 10 μm, in relation to the total weight of said powder component, from 1% to 15%, preferably from 5% to 10%, by weight of CDA in relation to the total weight of said powder component, from 1% to 10%, preferably from 1% to 5%, by weight of MCPM in relation to the total weight of said powder component, from 1% to 10%, preferably from 1% to 5%, by weight of DCPD in relation to the total weight of said powder component.

According to an embodiment, the powder component according to the invention comprises: from 70% to 80% by weight of α-TCP particles having an average size greater than or equal to 9 µm, preferably greater than or equal to 10 µm, in relation to the total weight of said powder component, from 1% to 15%, preferably from 5% to 10%, by weight of CDA in relation to the total weight of said powder component, and from 1% to 15%, preferably from 5% to 10%, by weight of DCPA in relation to the total weight of said powder component.

In the bone cement paste according to the invention, the powder component may further comprise at least one polysaccharide.

Polysaccharides are a class of carbohydrates, such as starch and cellulose, consisting of a number of monosaccharides joined by glycosidic bonds.

Cellulose ethers and their salts and mixtures thereof are preferred polysaccharides used in the powder component according to the invention, more preferably selected from the group consisting of hydroxypropylmethylcellulose (HPMC), and carboxymethylcellulose (CMC).

Preferably, the cellulose ethers amount varies between 0.1% and 5%, preferably between 1% and 3%, more preferably between 1% and about 2% by weight of the total amount of the powder component according to the invention.

Liquid Component

As mentioned above, the bone cement paste according to the invention comprises a liquid component comprising blood or a blood-derived product.

According to an advantageous embodiment, said liquid component comprises blood, and more preferably is blood.

Within the present application, the term "blood" refers to full blood. It thus includes white blood cells, red blood cells, and platelets.

Within the present application, the term "blood-derived-products" refers to plasmas, serums and previously described cells.

According to the invention, the liquid component may also include one or more of the following: saline, deionized water, dilute phosphoric acid, dilute organic acids (acetic, citric, succinic acid), sodium phosphate, sodium carbonate or bicarbonate, sodium alginate, sodium bicarbonate, sodium chondroitin sulphate a $Na_2HPO_4$ aqueous solution and/or a $Na_2HPO_4/NaH_2PO_4$ aqueous solution.

According to an embodiment, in the bone cement paste according to the invention, the liquid component (L)/powder component (P) ratio is between 0.3 and 0.7 mL/g, and preferably between 0.4 and 0.6 mL/g, and more preferably is 0.45 or 0.55 mL/g.

Cement

The present invention also relates to an apatitic calcium phosphate cement resulting from the setting of the bone cement paste as defined above.

In the context of the present invention, a "calcium phosphate cement" (CPC) is a solid composite material comprising or made of one or more calcium phosphates eventually with additional calcium salts which sets and hardens in the presence of the liquid component comprising blood. The term refers to the hardened material obtained after setting. Other additives may be included in small amounts to adjust the properties of the cement such as the setting time, the viscosity, reduce cohesion or swelling time, and/or induce macroporosity, and confer elasticity to the final hardened product.

An "apatitic" calcium phosphate cement crystallises in the hexagonal system having the formula $Ca_{5x}(PO_4)_{3x}$, $(OH, Cl, F)_x$ with $x \geq 1$.

In the context of the present invention, the "setting" of a cement means the hand-off self-hardening of the cement paste at ambient temperature, that is, depending on the environment, room temperature or body temperature.

The CPC according to the invention may also be named "CPC/blood composites".

According to an embodiment, the apatitic calcium phosphate cement of the invention further includes a contrasting agent for X-ray imaging or MRI, preferably a hydrosoluble contrasting agent, more preferably an aromatic polyiodine compound for X-ray imaging or a gadolinium-containing compound for MRI.

According to another embodiment, the apatitic calcium phosphate cement of the invention further includes a therapeutic agent (such as bisphosphonate or antibiotics) or a compound that will present a therapeutic effect (such as anticancer chimiokine or gallium).

The present invention also relates to an apatitic calcium phosphate cement obtainable by a process comprising the following steps: a) the preparation of a bone cement paste by mixing a powder component comprising α-TCP particles having an average size greater than or equal to 9 µm, preferably greater than or equal to 10 µm, and a liquid component comprising blood or a blood-derived product, said liquid component comprising preferably blood, and b) the setting of said bone cement paste.

Preferably, according to the invention, the setting time ranges from 10 minutes to 72 hours, preferably from 10 hours to 20 hours. In particular, the setting time according to the invention is of about 13 hours.

According to a preferred embodiment, the apatitic calcium phosphate cement according to the invention is injectable.

In the context of the present invention, an "injectable cement" or a "cement in a form suitable to be injected" refers to a cement paste which may be pushed through a needle with a diameter of a few millimetres, preferably between 1 mm and 5 mm, more preferably between 1 mm and 3 mm, most preferably between 2 mm and 3 mm. Particularly important parameters for injectable cements include the absence of large particles, a suitable viscosity as well as an appropriate setting time in vivo (at 37° C.).

Preferably, the apatitic phosphate cement according to the invention has a compressive strength between 2 MPa and 15 MPa.

Within the present application, the "compressive strength" is the maximal compressive stress supported by the cement sample upon failure.

According to an embodiment, the apatitic CPC according to the invention presents a compressive strength curve typical of ductile materials 72 hours after hardening. In particular, the CPC according to the invention presents a plastic behavior. That means that a hardened sample of this type of cement when submitted to a mechanical test (e.g. compressive strength test) will present a deformation profile before being fractured.

The CPC/blood composites according to the invention are advantageous in that the blood gives adhesion, cohesion and plasticity to the cement. The use of blood also significantly increases the osteoconduction and resorption in comparison with a cement without blood.

The CPC according to the invention are advantageously bioresorbable.

The term "bioresorbable" refers to the ability of a material to be resorbed in vivo. In the context of the present invention, "full" resorption means that no significant extracellular fragments remain. The resorption process involves elimination of the original implant materials through the action of body fluids, enzymes or cells.

Resorbed calcium phosphate may, for example, be redeposited as new bone mineral via osteoblastic cells action, or by being otherwise, reutilized within the body or excreted. "Strongly bioresorbable" means that a major part of the calcium phosphate implant is resorbed between one and five years. This delay depends not only on intrinsic features of the calcium phosphate implant but also on the implanted site, age of the patient, primary stability of implant etc. . . . .

Uses

The CPC according the invention can be used for dental and medical applications relating in particular to bone repair, augmentation, reconstruction, regeneration, and treatment of bone disease such as osteoporosis.

Additional medical applications include repair of bony defects, repair of bone fractures for spine fusion, prosthetic (hip, knee, shoulder or others) surgery revision, bone augmentation, and bone reconstructions.

The present invention also relates to the use of the apatitic phosphate cement as defined above, for filling a dental or bony defect.

Among dental or bony defects, one may cite the defects caused by trauma, surgery or pathology. In particular, the apatitic phosphate cement according to the invention may be used for treating osteoporosis or bone marrow lesions.

The CPC/blood composites according to the invention may be used in many applications, especially surgical applications.

The present invention also relates to an implant comprising an apatitic phosphate cement as defined above. In particular, this implant may be used to repair, restore, or augment bone, and/or to fill bony or tooth defects.

The present invention also relates to the use of an apatitic phosphate cement as defined above, for bone anchorage augmentation for the fixation of implants (screws).

The aim of such application is to have a densification of the bone surrounding a fixation implant for a patient with bad quality bone. For such application, the cement sets, and provides a mechanically more stable environment for the screw. This mode of action is even more efficient because of the plasticity (less brittle) of the CPC/blood composites which allows for the absorption of part of the mechanical stresses.

The use of the CPC/blood composite according to the invention is advantageous in that it avoids micro-movements, optimizes stability of the fixation implant, in the short term returns to weight bearing after surgery (mechanical augmentation) and in the longer term after the combined cement has remodeled into natural bone (biological augmentation).

For this application, the technique of implantation is as follows: thanks to its very high injectability, the cement according to the invention (associated with full blood) will penetrate and fill the trabecular bony structure in the area surrounding the fixation implant (screw). The fluidity (low viscosity) of the cement associated with full blood allows for a minimally invasive approach and delivery in this clinical application.

Placement prior to fixation implant: the cement with full blood is injected in the pre-hole. Upon screw implantation, the CPC/blood composite is pushed inside the trabecular structure around the screw, creating a denser area; or Placement after fixation implant placement, if the screw is cannulated and fenestrated (eg: N-Force, by Innovision). The cement with full blood is injected in the cannula of the screw, and will access and penetrate the trabecular structure through the fenestrations of the screw shaft.

The present invention also relates to the use of an apatitic phosphate cement as defined above, for the treatment of bone marrow lesions, especially by the implementation of the "subchondroplasty" technique. It thus relates to the apatitic phosphate cement as defined above, for its use for treating bone marrow lesions.

The aim of such application is to fill a cavity which has been created by lesions of the bone marrow, resulting in trabecular bone loss of volume and a related loss of mechanical resistance.

The mode of action is as follows: the cement sets, provides a mechanically more stable area at the implantation site and an increased mechanical resistance in compression.

The use of the CPC/blood composite according to the invention is advantageous in that the increased mechanical resistance in compression allows for the removal of the pain (curative short term effect) and prevents the collapse of the joint surface (preventive longer term action).

For this application, the technique of implantation is as follows: thanks to its very high injectability, the cement associated with full blood will penetrate and fill the trabecular bony structure in the area. The fluidity (low viscosity) of the cement associated with full blood allows for a minimally invasive approach and delivery in this clinical application.

The present invention also relates to the use of an apatitic phosphate cement as defined above, for promoting spine fusion inside intersomatic cages.

For the application of inter-body spinal fusion, the purpose is to fill an inter-body fusion cage in order to create a bone bridge to optimize the fusion. The mode of action is as follows: the cement sets once in place, and will resorb and remodel into natural bone, allowing for a bone bridge to be created.

The use of the CPC/blood composite according to the invention is advantageous in that it allows for a more stable fusion on the longer term. The particularly active osteogenic properties of this CPC when associated with full blood are a key success factor for an optimal bone reconstruction (quantity, quality and timing of reconstruction).

For this application, the technique of implantation is as follows: the fluidity (low viscosity) and cohesiveness of the cement associated with full blood allows for a minimally invasive approach and delivery in this clinical application. It can be placed into the fusion cage prior to implantation, or in a second step, after placement of the cage:

Placement prior to implantation of the fusion cage if the cage design does not allow for placement after implantation (absence of injection hole), or Placement after implantation of the fusion cage, if an injection hole is present (injection hole could be the positioner/handle hole).

The present invention also relates to a kit for the spinal fusion, comprising: a fusion cage, preferably in PEEK, and a bone cement powder comprising α-tricalcium phosphate (α-TCP) particles having an average size greater than or equal to 9 μm, preferably greater than or equal to 10 μm.

This kit is then used in combination with the liquid component as defined above for obtaining the bone cement paste and the corresponding cement after setting.

The present invention also relates to a kit for the spinal fusion, comprising: a fusion cage, preferably in PEEK, and a bone cement paste comprising a powder component comprising α-tricalcium phosphate (α-TCP) particles having an average size greater than or equal to 9 μm, preferably greater than or equal to 10 μm, and a liquid component comprising blood or a blood-derived product.

The present invention also relates to a method for promoting spine fusion inside intersomatic cages comprising the following steps: placing a fusion cage, preferably in PEEK, between two vertebral bodies, and injecting the bone cement paste as defined above inside said cage.

This method is carried out as explained above.

It is advantageous over the known methods in that the step for placing the fusion cage is carried out before the injection step. Indeed, to date, there is no known method where the cage is placed before the injection of the cement. The known methods involve the placement of a fusion cage filled with autologous bone. Moreover, these prior art methods have a high failure ratio.

The invention will be further illustrated in view of the following figures and examples.

EXAMPLES

Materials

The apatitic calcium phosphate cements (CPC) used in this study were obtained from Graftys SA (Aix-en-Provence, France).

Graftys® HBS

Graftys® HBS is a mixture of 78 wt. % α-tricalcium phosphate (α-TCP) ($Ca_3(PO_4)_2$) (average equivalent diameter: 12 μm), 5 wt. % dicalcium phosphate dihydrate (DCPD) ($CaHPO_4$, $2H_2O$), 5 wt. % monocalcium phosphate monohydrate (MCPM) ($Ca(H_2PO_4)_2$, $H_2O$), 10 wt. % CDA ($Ca_{10-x}[\ ]_x(HPO_4)y(PO_4)_{6-y}(OH)_{2-z}[\ ]_z$), 2 wt. % hydroxypropyl methyl cellulose (HPMC) (E4 M®, Colorcon-Dow Chemical, Bougival, France).

The liquid phase consists of a 5 wt. % $Na_2HPO_4$ aqueous solution (liquid/powder ratio=0.5 mL·$g^{-1}$).

Graftys® Quickset

Graftys® Quickset is a mixture of 78 wt. % α-TCP (average equivalent diameter: 5 μm), 10 wt. % anhydrous dicalcium phosphate (DCPA) ($CaHPO_4$), 10 wt. % CDA, 2 wt. % HPMC.

The liquid phase consists of a 0.5 wt. % $Na_2HPO_4$ aqueous solution (liquid/powder ratio=0.45 mL·$g^{-1}$).

Graftys® HBS and Graftys® Quickset cement paste samples were prepared by mixing 8 g of the powdered preparation with their respective liquid phase for 2 min to ensure the homogeneity of the obtained paste before analysis.

The same conditions were applied for the preparation of the corresponding blood/CPC composites, except that the liquid phase was fully replaced by ovine freshly harvested blood.

Methods

The high frequency impedance measurements were recorded, between 0.4 and 100 MHz, with a HP 4194 A impedance/gain-phase analyser (Hewlett-Packard), using an experimental setup allowing to concomitantly perform complex impedance and Gillmore needles measurements at 37° C., as reported previously (Despas, C.; Schnitzler, V.; Janvier, P.; Fayon, F.; Massiot, D.; Bouler, J. M.; Bujoli, B.; Walcarius, A. High-frequency impedance measurement as a relevant tool for monitoring the apatitic cement setting reaction *Acta Biomater* 2014, 10, 940).

The experimental device was completed by a computer allowing automatic data acquisition and real-time calculation of the complex impedance, Z* from which the dielectric permittivity, ε' (related to dipole variation), and dielectric losses, ε" (related to the motion of free charges), were computed (Thiebaut, J. M.; Roussy, G.; Chlihi, K.; Bessiere, J. Dielectric study of the activation of blende with cupric ions *Journal Of Electroanalytical Chemistry* 1989, 262, 131).

The initial setting time ($t_i$) is defined as the time elapsed until the small Gillmore needle (diameter 2.12 mm, weight 113.4 g) fails to indent the surface of the sample, while the final setting time ($t_f$) is the corresponding value when using the large Gillmore needle (diameter 1.06 mm, weight 453.6 g)

Compressive strength measurements and texture analyses versus time were performed using a AMETEK LS5 texture analyzer. The compression force necessary to extrude the cement paste samples from a syringe (inner diameter of the cartridge 8.2 mm, inner diameter of the exit hole 1.7 mm) was measured versus time at regular intervals (ca. every 3 min), while keeping the extrusion rate constant (0.1 mm $s^{-1}$).

In Vivo Implantation of Graftys® HBS and Graftys® Quickset CPC Versus Their Respective Blood Composites Animals and Surgical Procedures All animal handling and surgical procedures were conducted according to European Community guidelines for the care and use of laboratory animals (DE 86/609/CEE) and approved by the local Veterinary School ethical committee.

The tested biomaterials have been implanted bilaterally for 4 weeks and 8 weeks respectively at the distal end of 24 mature female New Zealand White rabbit (3-3.5 kg) femurs. A lateral arthrotomy of the knee joint was performed and a cylindrical 6×10 mm osseous critical-sized defect was created at the distal femoral end. After saline irrigation, the osseous cavity was carefully dried and filled with the tested calcium phosphate cements. Twelve rabbits were implanted with Graftys® HBS versus its blood composite, and the same number with Graftys® Quickset versus its blood composite.

Two-Dimensional Histomorphometric SEM Analysis and Histological Studies

Implanted and control samples were classically prepared for SEM-based histomorphometry and qualitative histological examination on light microscopy [For details see Gauthier et al. 2005, Biomaterials). Undecalcified serial 7 mm sections of each sample were stained using Movat's pentachrome staining. This bone specific staining is perfectly adapted to distinguish mineral (yellow-green), osteoid tissue (red line) and cement (blue) (Verron, E.; Gauthier, O.; Janvier, P.; Pilet, P.; Lesoeur, J.; Bujoli, B.; Guicheux, J.; Bouler, J. M. In vivo bone augmentation in an osteoporotic environment using bisphosphonate-loaded calcium deficient apatite *Biomaterials* 2010, 31, 7776). To analyze more specific tissue components, hematoxylin-eosin was performed. Samples were observed with a polarized light microscope (Axioplan2®, Zeiss, Germany).

Statistical Analysis

SEM-Based Histomorphometry for the Rabbit Study

The means for each of the 8 experimental groups (N=6) were calculated and statistical difference between different groups and between different treatments were evaluated by analysis of variance (ANOVA). The threshold for significance was set at 95% (p=0.05).

Example 1

Setting Times of the Compositions

The setting time of a composition according to the invention was compared with prior art compositions without blood and with a composition with blood and a CPC wherein the α-TCP particles have an average size particle of less than 10 μm.

Blood was introduced into the composition of two commercially available injectable apatitic cements (Graftys® Quickset [abbreviated as QS] and Graftys® HBS [abbreviated as HBS]) showing marked differences in their setting time (see Table 1). For that purpose, the liquid phase (0.5 wt. % $Na_2HPO_4$ and 5 wt. % $Na_2HPO_4$, respectively) was fully replaced by ovine blood stabilized by addition of sodium citrate (3.2 wt. %), while keeping all other parameters fixed.

The potential influence of blood on the CPC setting reaction at body temperature was first investigated using the Gillmore needles standard test method, which allows determining the initial ($t_i$) and final ($t_f$) setting times by measuring the change in the material's penetration resistance. While a 4 minutes increase in the initial setting time was observed upon addition of blood in the fast setting formulation (QS), the Gillmore method failed to determine the $t_i$ value when blood was used as the liquid phase in HBS, since no 'visible indentation' could be observed, due to the elastic texture of the resulting composite.

variation of both of these parameters turned out to be strongly correlated to the chemical reactions taking place during the setting process, in contrast to the Gillmore conventional standard method which shows significant limitations in some cases, especially when additives are present in the cement paste.

Therefore, the impedance response of QS and HBS, compared to their analogues combined to blood, was recorded and the evolution of the ε' and ε" experimental values during the setting reaction are presented in FIG. 1. As shown previously, the sharp variations of the ε' and ε" curves (↑ε' and ↓ε" values) can be assigned to the conversion of α-TCP into CDA on the particles surface.

In the case of the fast setting formulation (comparative data with QS), substitution of the liquid phase by blood did not result in a significant change in the evolution of the dielectric permittivity and dielectric losses versus reaction time, although the initiation of CDA precipitation was slightly shifted towards longer times for the blood-containing composition. This is in sharp contrast with the case of HBS for which the setting reaction was drastically retarded (ca. 13 hours) in the presence of blood as the liquid phase (corresponding to a composition according to the invention).

The results concerning QS are shown in FIG. 1A and the results concerning HBS are shown in FIG. 1B.

Example 2

Injectability of the Compositions

Texture analyses are relevant to probe the injectability of calcium phosphate pastes and assess their behavior under pressure (Ginebra, M. P.; Rilliard, A.; Fernandez, E.; Elvira, C.; San Roman, J.; Planell, J. A. Mechanical and rheological improvement of a calcium phosphate cement by the addition of a polymeric drug *J Biomed Mater Res* 2001, 57, 113).

TABLE 1

Characteristic parameters resulting from the monitoring of the setting reaction of the studied cements at 37° C., using Gillmore needles (first line) or high frequency impedance (four next lines), as a function of the liquid phase (phosphate buffer versus blood).

| | | QS (comparative) | | HBS | |
|---|---|---|---|---|---|
| | Liquid phase | 0.5 wt. % $Na_2HPO_4$ | blood | 5 wt. % $Na_2HPO_4$ (comparative) | Blood (invention) |
| Gillmore determination | $t_i$ (min) | 7 ± 1 | 12 ± 2 | 15 ± 2 | not measurable |
| HF impedance determination | $t_1$(ε') (min) | <6[a] | <4[a] | <4[a] | 900 |
| | $t_1$(ε") (min) | <6[a] | <4[a] | <4[a] | 900 |
| | $t_2$(ε') (min) | 5 | 270 | 40 | 1100 |
| | $t_2$(ε") (min) | 10 | 550 | 37 | 1200 |

[a]Cement hardening began before the first measurable dielectric values (see Materials and methods)

The article of Despas, C.; Schnitzler, V.; Janvier, P.; Fayon, F.; Massiot, D.; Bouler, J. M.; Bujoli, B.; Walcarius, A. High-frequency impedance measurement as a relevant tool for monitoring the apatitic cement setting reaction *Acta Biomater* 2014, 10, 940 reports the development of a relevant and general method based on high frequency impedance measurements, for the in situ monitoring of the alpha-tricalcium phosphate (α-TCP) to calcium-deficient hydroxyapatite (CDA) transformation which is the driving force of the hardening process of apatitic CPCs.

Figure 2:
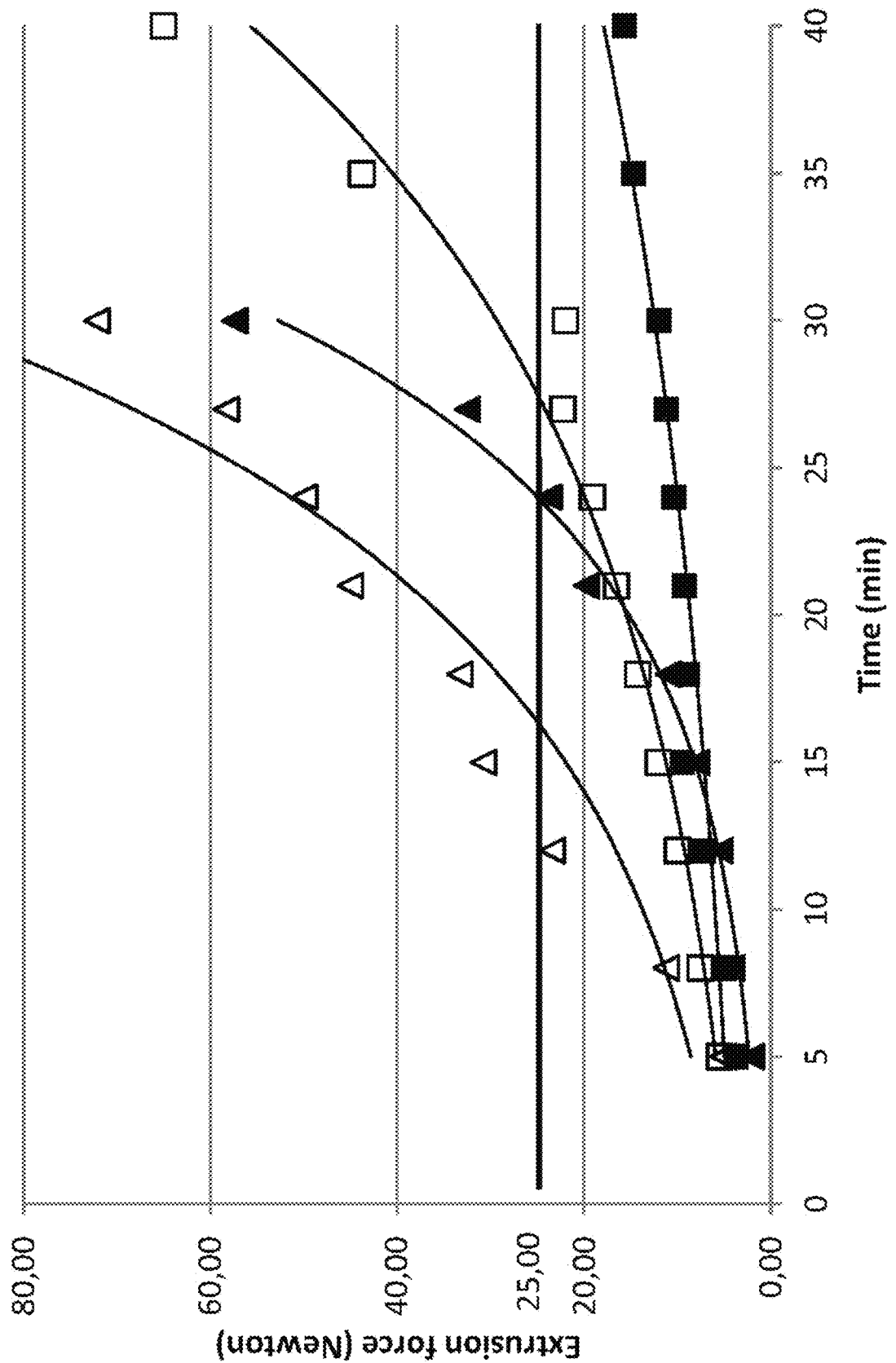
FIG. 2: Force necessary for extrusion of the cement paste as a function of time at 20° C. for QS (Δ) (comparative composition) and its blood-containing analogue (comparative composition) (▲), HBS (□) (comparative composition) and its blood-containing analogue (■) (composition according to the invention).

From the complex impedance data, the dielectric permittivity (ε', related to dipole variation) and dielectric losses (ε", related to the motion of free charges) can be computed. The For both cements without blood, extrusion forces rapidly reach a plateau, followed by a very sharp increase (FIG. 2), which corresponds to the beginning of the hardening process.

Substitution of the liquid phase by blood led to more injectable materials, especially for the HBS-based composition according to the invention, in full agreement with the variation of setting properties evidenced by impedance measurements (as mentioned in example 1).

In all cases, the increase in the force necessary for extrusion of the cement paste was not due to phase separation, since the full content of the syringe could be injected.

Example 3

Mechanical Properties of the Compositions

Figure 3:
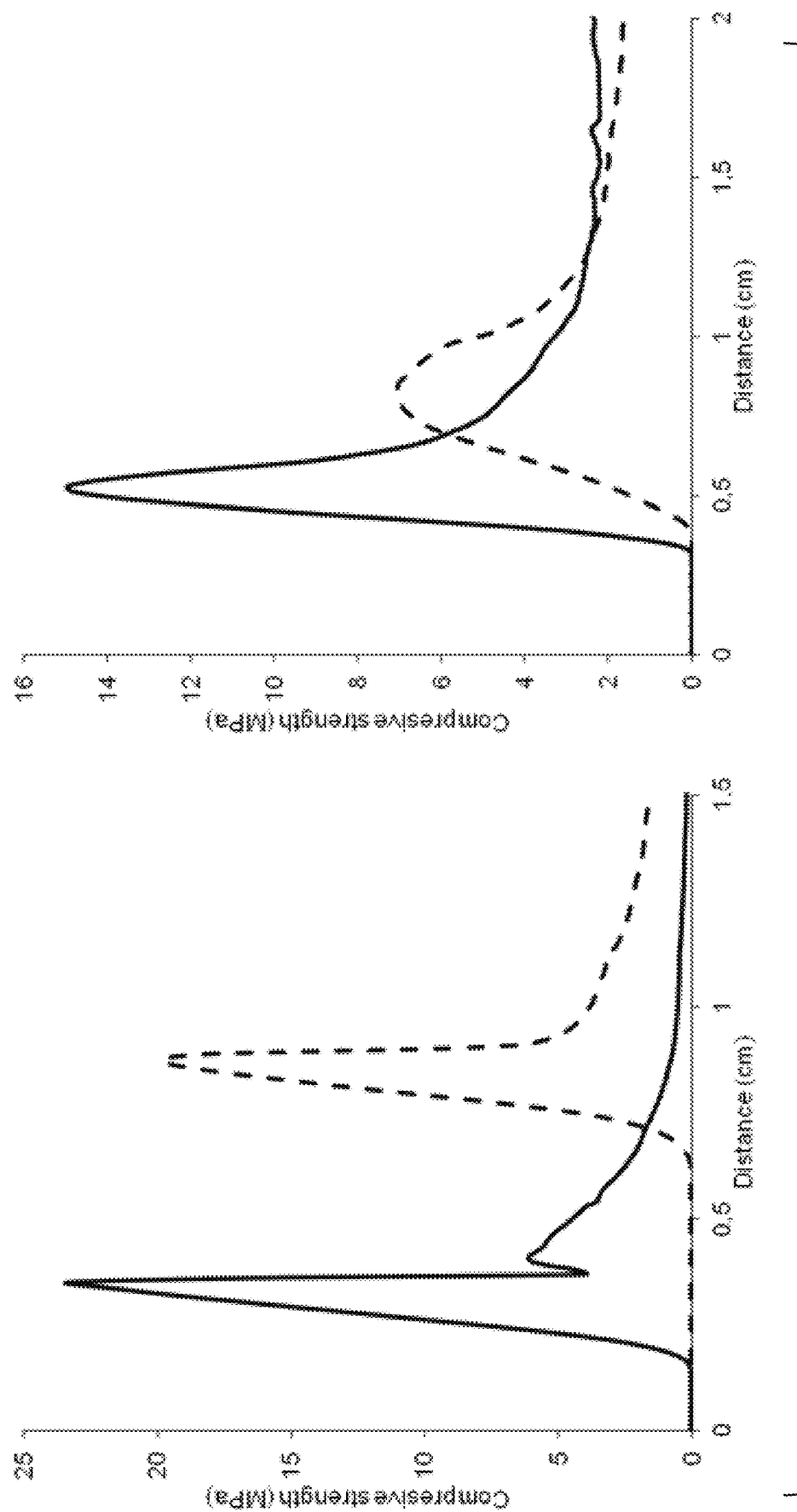
FIG. 3: Compressive strength of the cement formulations after a setting time of 72 hours: (right) QS (straight line) and its blood-containing analogue (dotted line), (left) HBS (straight line) and its blood-containing analogue (dotted line).

The introduction of blood into the CPC compositions did not result in significant changes in the mechanical properties of the QS formulation. Indeed, for these comparative compositions, the compressive strength after a setting time of 72 hours was in the similar range in the presence (21±2 MPa) or absence (25±5 MPa) of blood, with a fragile behaviour (see FIG. 3 right). This observation is consistent with the very limited effect of blood on the complex impedance response.

On the contrary, a dramatic change was observed for the composition according to the invention (HBS formulation), since when combined to blood the compressive strength after a setting time of 72 hours considerably dropped (6.4±0.1 MPa for the composition of the invention versus for the 14±2 MPa for the comparative composition without blood).

Interestingly, the stiffness was less than HBS, accounting for a more plastic behaviour of the sample (see FIG. 3 left) from 72 hours to 336 hours post mixture.

Example 4

Resorption Properties of the Compositions

Quantitative SEM Histomorphometry

Figure 4:
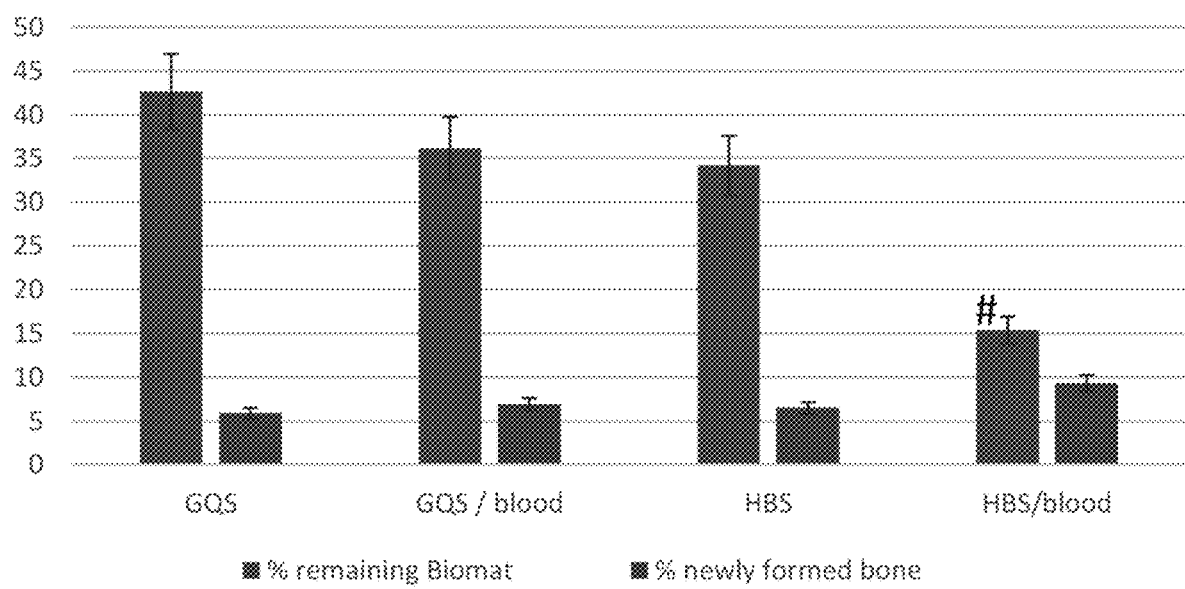
FIG. 4: Comparative quantitative analysis of newly formed bone and remaining implanted materials from SEM measurements.
Figure 4:
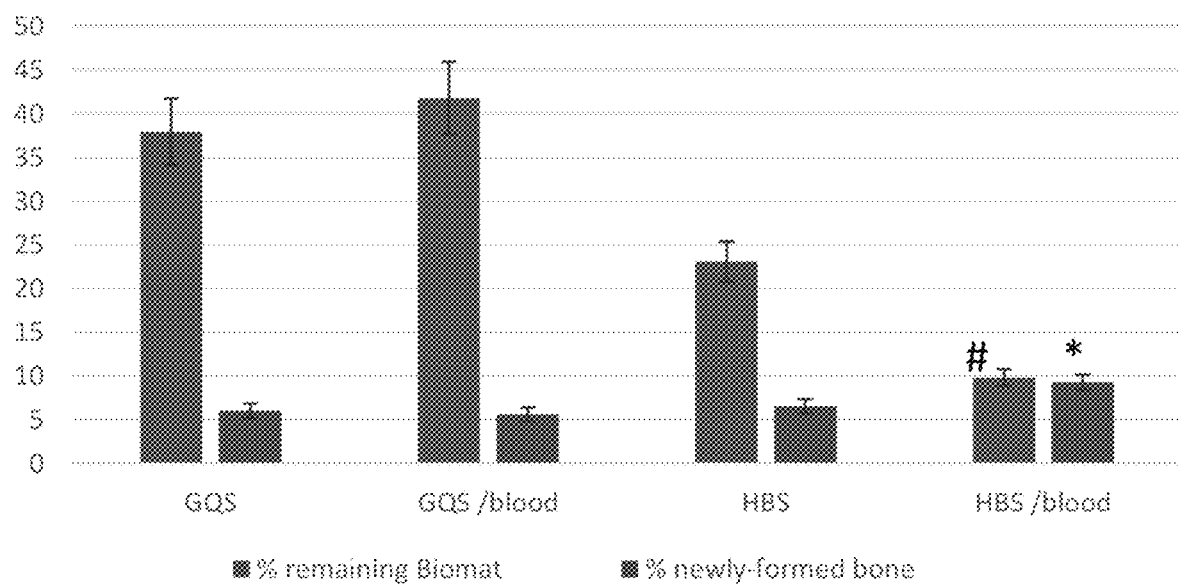

Four weeks after implantation (as explained above), all groups showed an equivalent new bone formation and only the compositions according to the invention (HBS/blood) presented a significantly higher material degradation compared to the other groups ($p<0.0001$) (FIG. 4A). After 12 weeks, the compositions according to the invention (HBS/blood composition) underwent significantly higher material degradation ($p<0.0001$) and led to higher new bone formation ($p<0.01$), when compared to the other groups (FIG. 4B).

Example 5

In Vivo Response Comparisons in Ovine Spine Fusion of CPC, CPC Blood Composite and Autograft An in vivo study was conducted in sheep to evaluate the capacity of the compositions according to the invention (in comparison with a composition without blood) in promoting spine fusion inside intersomatic cages 3 months after implantation. Autograft was used as positive control.

Compositions

The comparative CPC is a mixture of 78 wt. % α-TCP, 10 wt. % anhydrous dicalcium phosphate (DCPA) ($CaHPO_4$), 10 wt. % CDA, 2 wt. % HPMC. Average size of inorganic powder particles was 6 μm. The liquid phase consists of a 0.5 wt. % $Na_2HPO_4$ aqueous solution (liquid/powder ratio=0.45 mL·$g^{-1}$).

The composition of the invention is a mixture of 78 wt. % α-tricalcium phosphate (α-TCP) ($Ca_3(PO_4)_2$), 5 wt. % dicalcium phosphate dihydrate (DCPD) ($CaHPO_4$, $2H_2O$), 5 wt. % monocalcium monohydrate (MCPM) ($Ca(H_2PO_4)_2$, $H_2O$), 10 wt. % CDA ($Ca_{10-x}[\ ]_x(HPO_4)y(PO_4)_{6-y}(OH)_{2-z}[\ ]_z$), 2 wt. % hydroxypropyl methyl cellulose (HPMC) (E4 M®, Colorcon-Dow Chemical, Bougival, France). Average size of α-TCP was 12 μm. The liquid phase consists of fresh ovine blood stabilized by addition of sodium citrate (3.2 wt. %) (liquid/powder ratio=0.5 mL·$g^{-1}$).

An autologous corticocancellous bone graft was harvested from the distal femoral epiphysis site.

Intersomatic Cages

Polyether-ether-ketone cages LDR-ROI-C® (14×14×6 mm) were placed after discectomy between L2/L3 and L4/L5 ovine intervertebral levels. Autograft was crushed with a rongeur and then packed into the fusion cage before its impaction. The compositions according to the invention and the comparative compositions were injected inside cages after impaction. Three months after implantation, animals were euthanatized by intravenous injection of 20 ml of pentobarbital (Doléthal®, Vétoquinol S. A., France) through a catheter placed into the jugular vein. Lumbar segments from L1 to L5 were then harvested after dissection from the surrounding soft tissues, submitted to XRay imaging and immediately placed in a 10% neutral formol solution. L2/L3 and L4/L5 intervertebral specimen were fixed at 4° C. for 24 h in neutral formol solution, pH 7.2, and then dehydrated in increasing ethanol baths from 70% to 100% for 3 days each. Resin impregnation was then performed by using methylmethacrylate.

Results

Figure 5:
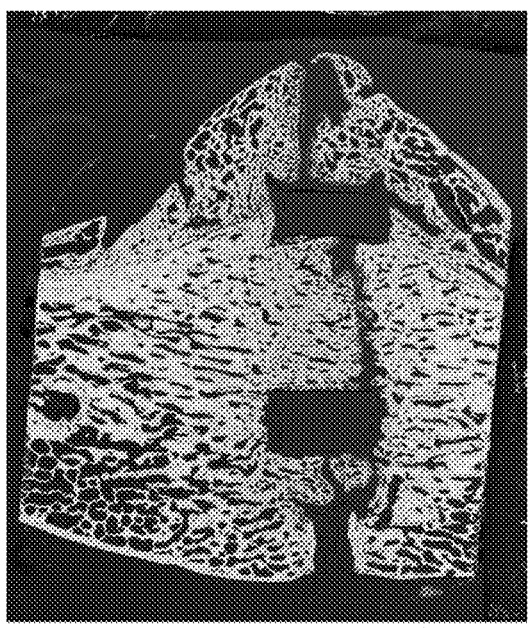
FIG. 5: SEM micrographs of comparative composition (a), composition according to the invention (b), and autograft (c).
Figure 5:
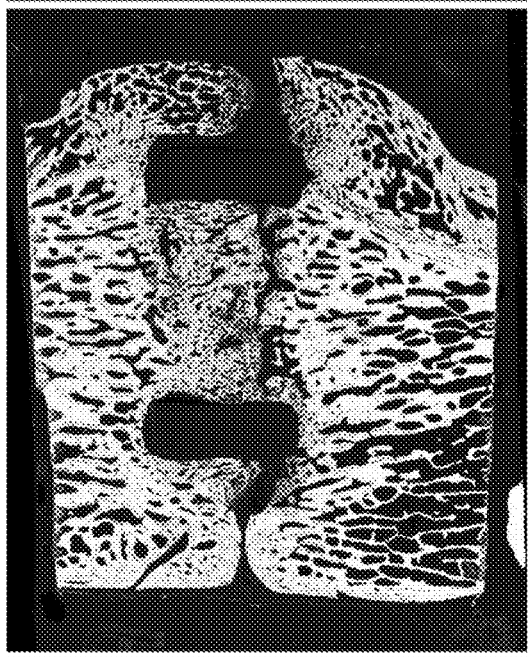
Figure 5:
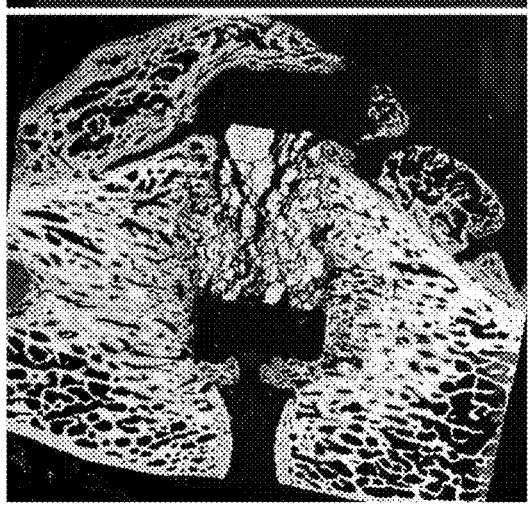
Figure 6:
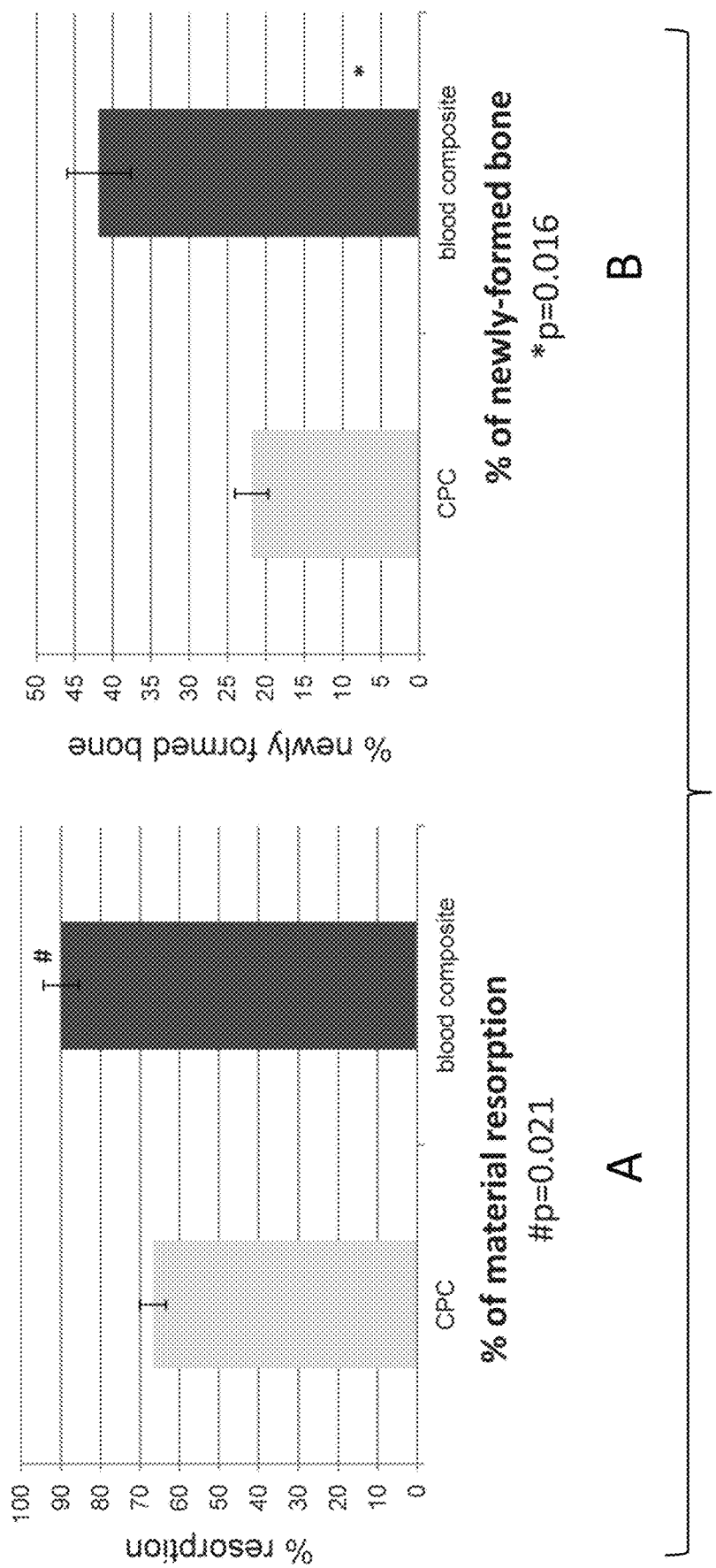
FIG. 6: 3D quantifications inside cage volumes (500 $mm^3$—μCT analysis—resolution 12 μm).

SEM observation (FIG. 5) and 3D-μCT quantitative analysis (FIG. 6) show that: comparison of the composition of the invention with the comparative composition: a strong increased resorption rate and consequently an increased new bone formation at 3 months postoperatively; and comparison of the composition of the invention with the autograft: a comparative fusion rate at 3 month postoperatively.

After 12 weeks of implantation the blood composite cement showed a better resorption rate (+22%) compared to control. Quality of newly formed bone is very similar for both tested CPCs with an excellent bone/implant osteocoalescent interface.

Example 6

Setting Times and Compressive Strength of a Composition According to the Invention The setting time of a composition according to the invention was compared with prior art compositions without blood and with a composition with blood.

The apatitic calcium phosphate cements (CPC) used in this study were obtained from Graftys SA (Aix-en-Provence, France).

Graftys® GQSb10h is a mixture of 78 wt. % α-TCP (average equivalent diameter of particles: 9.1 μm), 10 wt. % anhydrous dicalcium phosphate (DCPA) ($CaHPO_4$), 10 wt. % CDA, and 2 wt. % HPMC.

The liquid phase (liquid/powder ratio=0.45 mL·$g^{-1}$) consists of:

either 0.5 wt. % $Na_2HPO_4$ aqueous solution, or 5 wt. % $Na_2HPO_4$ aqueous solution, or ovine freshly harvested blood.

Graftys® GQSb10h cement paste samples were prepared by mixing 8 g of the powdered preparation with their respective liquid phase for 2 min to ensure the homogeneity of the obtained paste before analysis.

The measured properties are the following:

| Liquid component | Na$_2$HPO$_4$ 0.5% | Na$_2$HPO$_4$ 5% | Fresh ovine blood |
|---|---|---|---|
| Initial setting time (min) | 29 ± 2 | 14 ± 1 | 26 ± 1 |
| Compressive strength at 6 h (MPa) | 1 ± 0 | 3 ± 1 | 0.5 ± 0 |
| Compressive strength at 24 h (Mpa) | 21 ± 3 | 7 ± 0 | 11 ± 1 |
| Compressive strength at 72 h (MPa) | 26 ± 1 | 17 ± 2 | 15 ± 2 |
| Compressive strength at 336 h (MPa) | 32 ± 2 | 24 ± 2 | 21 ± 1 |

Blood addition effect as observed in examples 1, 2 and 3 observed with HBS composition is here observed on a QS composition presenting a powder average size >9 μm.

Example 7 (Comparative)

Comparison of the Properties of a Composition According to the Invention (with Blood as Liquid Component) with the Properties of a Composition with Plasma as Liquid Component Graftys® HBS Vs Graftys® HBS+Plasma Graftys® HBS is a mixture of 78 wt. % α-tricalcium phosphate (α-TCP) (Ca$_3$(PO$_4$)$_2$) (average equivalent diameter of particles: 12 μm), 5 wt. % dicalcium phosphate dihydrate (DCPD) (CaHPO$_4$, 2H$_2$O), 5 wt. % monocalcium phosphate monohydrate (MCPM) (Ca(H$_2$PO$_4$)$_2$, H$_2$O), 10 wt. % CDA (Ca$_{10-x}$[ ]$_x$(HPO$_4$)$_y$(PO$_4$)$_{6-y}$(OH)$_{2-z}$[ ]$_z$), 2 wt. % hydroxypropyl methyl cellulose (HPMC) (E4 M®, Colorcon-Dow Chemical, Bougival, France).

The liquid phase (liquid/powder ratio=0.5 mL·g$^{-1}$) consists of:
either 5 wt. % Na$_2$HPO$_4$ aqueous solution,
or plasma obtained from ovine freshly harvested blood.

Plasma was obtained after blood centrifugation for 15 min at 1,800 g at room temperature (RT).

Graftys® HBS cement paste samples were prepared by mixing 8 g of the powdered preparation with their respective liquid phase for 2 min to ensure the homogeneity of the obtained paste before analysis.

The measured properties are as shown in the below table:

| Liquid component | Na$_2$HPO$_4$ 5% | Fresh ovine plasma |
|---|---|---|
| Initial setting time (min) | 15 ± 2 | Not measurable |
| Compressive strength at 72 h (MPa) | 14 ± 2 | Not measurable |

Replacing HBS liquid component by plasma does not provide suitable cement for bone grafting surgery in term of both setting time and compressive strength.

Example 8

Compositions Comprising a Therapeutic Agent, and Optionally a Contrast Agent

Graftys® MIA is a mixture of 78 wt. % α-tricalcium phosphate (α-TCP) (Ca$_3$(PO$_4$)$_2$) (average equivalent diameter of particles: 12 μM), 5 wt. % dicalcium phosphate dihydrate (DCPD) (CaHPO$_4$, 2H$_2$O), 5 wt. % monocalcium phosphate monohydrate (MCPM) (Ca(H$_2$PO$_4$)$_2$, H$_2$O), 10 wt. % CDA (Ca$_{10-x}$[ ]$_x$(HPO$_4$)$_y$(PO$_4$)$_{6-y}$(OH)$_{2-z}$[ ]$_z$), partially loaded with Alendronate; 2 wt. % hydroxypropyl methyl cellulose (HPMC) (E4 M®, Colorcon-Dow Chemical, Bougival, France). The solid phase contains 0.56 mg of Alendronate per g of cement.

The liquid phase (liquid/powder ratio=0.5 mL·g$^{-1}$) consists of:
either 5 wt. % Na$_2$HPO$_4$ aqueous solution,
or ovine freshly harvested blood,
or ovine freshly harvested blood+Xenetix (168 mG of Iodine/mL of blood).

Graftys® HBS cement paste samples were prepared by mixing 8 g of the powdered preparation with their respective liquid phase for 2 min to ensure the homogeneity of the obtained paste before analysis.

The measured properties are as shown in the below table:

| Liquid component | Na$_2$HPO$_4$ 5% | Fresh ovine blood | Fresh ovine blood + Xenetix ® |
|---|---|---|---|
| Initial setting time (min) | <15 | 22 ± 2 | 39 ± 5 |
| Compressive strength at 72 h (MPa) | 18 ± 2 | 15 ± 2 | 10 ± 2 |

Adding Xenetix in blood increases cement setting time and decreases its compressive strength. However those two handling properties look still compatible with bone grafting surgery.

What is claimed is:

1. A method for promoting spine fusion inside intersomatic cages, comprising the following steps:
   placing a fusion cage between two vertebral bodies, and
   injecting a bone cement paste inside said fusion cage, said bone cement paste comprising a powder component and a liquid component comprising blood;
   wherein the powder component comprises in relation to the total weight of said powder component:
   from 70% to 80% by weight of α-tricalcium phosphate (α-TCP) particles having an average size greater than or equal to 9 μm, wherein said average size is the mean equivalent diameter of said particles measured by LASER diffraction analysis,
   from 1% to 10% by weight of monocalcium phosphate monohydrate (MCPM),
   from 1% to 10% by weight of dicalcium phosphate dihydrate (DCPD),
   from 5% to 15% by weight of calcium-deficient apatite (CDA), and
   from 0.1% to 5% by weight of a cellulose ester; and
   wherein the liquid component (L)/powder component (P) ratio is between 0.3 and 0.7 mL/g; and
   wherein the bone cement paste has a setting time ranging from 10 minutes to 72 hours.

2. The method of claim 1, wherein the liquid component consists of blood.

3. The method of claim 1, wherein the powder component further comprises at least one calcium phosphate compound other than α-TCP, MCPM, DCPD and CDA.

4. The method of claim 3, wherein the calcium phosphate compound is selected from the group consisting of hydroxyapatite (HA), amorphous calcium phosphate (ACP), monocalcium phosphate anhydrous (MCPA), dicalcium phosphate anhydrous (DCPA), β-tricalcium phosphate (β-TCP), tetracalcium phosphate (TTCP), and mixtures thereof.

5. The method of claim 1, wherein the liquid component (L)/powder component (P) ratio is between 0.4 and 0.6 mL/g.

6. The method of claim 1, wherein the α-tricalcium phosphate (α-TCP) particles have an average size greater than or equal to 10 µm.

7. The method of claim 1, wherein the cellulose ester is selected from the group consisting of hydroxypropylmethylcellulose (HPMC) and carboxymethylcellulose (CMC).

8. The method of claim 1, wherein the powder component further comprises at least one therapeutic agent.

9. The method of claim 1, wherein the liquid component further comprises at least one contrasting agent for X-ray imaging or MRI.

10. The method of claim 1, wherein the method further comprises a step of setting the bone cement paste, thereby obtaining an apatitic calcium phosphate cement inside said fusion cage; and wherein said apatitic calcium phosphate cement has a compressive strength 72 h after hardening between 2 MPa and 15 MPa.

* * * * *